United States Patent
Aeschlimann et al.

(10) Patent No.: US 6,203,746 B1
(45) Date of Patent: Mar. 20, 2001

(54) PROCESS FOR THE TREATMENT OF CELLULOSE FIBRES

(75) Inventors: Peter Aeschlimann, Allschwil (CH); Bernhard Müller, Efringen-Kirchen (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/289,317

(22) Filed: Apr. 9, 1999

(30) Foreign Application Priority Data

Apr. 14, 1998 (EP) .................................. 98810315
May 19, 1998 (CH) .................................. 1096/98

(51) Int. Cl.[7] ............................ D01F 2/02; D06M 13/358
(52) U.S. Cl. ............................................... 264/340
(58) Field of Search .............................................. 264/340

(56) References Cited

U.S. PATENT DOCUMENTS

| | | | |
|---|---|---|---|
| 5,786,475 | 7/1998 | Fuso et al. | 544/198 |
| 5,795,522 * | 8/1998 | Firgo et al. | 264/187 |

FOREIGN PATENT DOCUMENTS

| | | |
|---|---|---|
| 19611668 | 10/1997 | (DE) . |
| 197 20 683 | 11/1997 | (DE) . |
| 538977 | 4/1993 | (EP) . |
| 1483666 | 8/1977 | (GB) . |
| 94/09191 | 4/1994 | (WO) . |

OTHER PUBLICATIONS

Abstract for DE 19611668 (Published Oct. 2, 1997).
Abstract for DE 19720683 (Published Nov. 27, 1997).

* cited by examiner

Primary Examiner—Leo B. Tentoni
(74) Attorney, Agent, or Firm—Kevin T. Mansfield

(57) ABSTRACT

The present invention relates to a process for the treatment of lyocell cellulose fibers which comprises treating the lyocell cellulose fibers with at least one compound of the formula

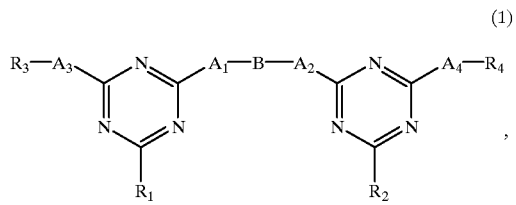

(1)

wherein $R_1$ and $R_2$ are each independently of the other halogen or a sulfo-substituted phenylamino radical, at least one of the two substituents $R_1$ and $R_2$ being halogen, $R_3$ and $R_4$ are each independently of the other unsubstituted phenyl or phenyl substituted by $C_1$–$C_4$alkyl, $C_1$–$C_4$alkoxy, acylamino, sulfo, —$SO_2$—CH=$CH_2$, —$SO_2$—$CH_2CH_2$—$OSO_3H$, —NH—CO—CBr=$CH_2$ or by —NH—CO—CHBr—$CH_2Br$, $A_1$ and $A_2$ are each independently of the other —O—, —S— or —$NR_5$—, wherein $R_5$ is hydrogen or $C_1$–$C_4$alkyl, $A_3$ and $A_4$ are each independently of the other —O—, —S— or —$NR_5$—, or —$A_3$—$R_3$ is halogen and/or —$A_4$—$R_4$ is halogen, wherein $R_5$ is hydrogen or $C_1$–$C_4$alkyl and B is an aromatic bridge member, or —$A_1$—B—$A_2$— is a bridge member of the formula —NH—$CH_2$—CH($CH_3$)—NH—, with the proviso that the compound of formula (1) must contain at least one dihalotriazine radical, at least two monohalotriazine radicals or at least one substituent, but preferably at least two identical or different substituents, from the group consisting of —$SO_2$—CH=$CH_2$, —$SO_2$—$CH_2CH_2$—$OSO_3H$, —NH—CO—CBr=$CH_2$ and —NH—CO—CHBr—$CH_2Br$.

7 Claims, No Drawings

PROCESS FOR THE TREATMENT OF CELLULOSE FIBRES

The present invention relates to a process for reducing the fibrillation tendency in lyocell cellulose fibres.

"Lyocell" designates fibres that have been obtained by a process in which the cellulose is dissolved in an organic solvent, in a combination of an organic solvent and an inorganic salt, or in an aqueous salt solution, and is then spun from the resulting solution.

The usefulness of flat goods, for example textile materials, produced from such fibres as severely limited, however, as a result of the pronounced tendency of those fibres to fibrillate in the wet state. "Fibrillation" is to be understood as meaning the breaking up of the wet fibres in the longitudinal direction when subjected, for example, to mechanical stress, to the extent that fibrils become detached along the surface of the fibres, giving the fibres a hairy or furry appearance. In addition, a fabric produced from such fibres suffers a pronounced loss in colour intensity after a few washes.

A need therefore exists for a process that reduces or completely prevents fibrillation in lyocell fibres.

Surprisingly, it has been found that by means of the process according to the invention the fibrillation tendency of the treated lyocell fibres is substantially reduced.

The present invention accordingly relates to a process for the treatment of lyocell cellulose fibres which comprises treating the lyocell cellulose fibres with at least one compound of the formula

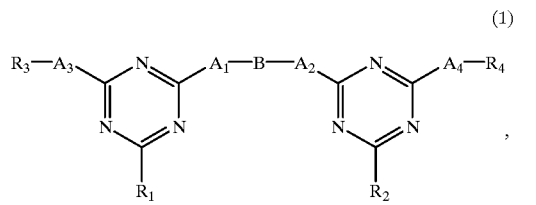

(1)

wherein $R_1$ and $R_2$ are each independently of the other halogen or a sulfo-substituted phenylamino radical, at least one of the two substituents $R_1$ and $R_2$ being halogen, $R_3$ and $R_4$ are each independently of the other unsubstituted phenyl or phenyl substituted by $C_1$-$C_4$alkyl, $C_1$-$C_4$alkoxy, acylamino, sulfo, —$SO_2$—$CH=CH_2$, —$SO_2$—$CH_2CH_2$—$OSO_3H$, —NH—CO—$CBr=CH_2$ or by —NH—CO—$CHBr$—$CH_2Br$, $A_1$ and $A_2$ are each independently of the other —O—, —S— or —$NR_5$—, wherein $R_5$ is hydrogen or $C_1$-$C_4$alkyl, $A_3$ and $A_4$ are each independently of the other —O—, —S— or —$NR_5$—, or —$A_3$—$R_3$ is halogen and/or —$A_4$—$R_4$ is halogen, wherein $R_5$ is hydrogen or $C_1$-$C_4$alkyl and B is an aromatic bridge member, or —$A_1$—B—$A_2$— is a bridge member of the formula —NH—$CH_2$—$CH(CH_3)$—NH—, with the proviso that the compound of formula (1) must contain at least one dihalotriazine radical, at least two monohalotriazine radicals or at least one substituent, but preferably at least two identical or different substituents, from the group consisting of —$SO_2$—$CH=CH_3$, —$SO_2$—$CH_2CH_2$—$OSO_3H$, —NH—CO—$CBr=CH_2$ and —NH—CO—$CHBr$—$CH_2Br$.

$C_1$-$C_4$Alkyl as a phenyl substituent in $R_3$ and $R_4$ is methyl, ethyl, n-propyl, isopropyl, n-butyl, sec-butyl, isobutyl or tert-butyl.

As $C_1$-$C_3$alkyl $R_5$ is methyl, ethyl, propyl, isopropyl, n-butyl, sec-butyl, isobutyl or tert-butyl.

$C_1$-$C_4$Alkoxy as a phenyl substituent in $R_3$ and $R_4$ is, for example, methoxy, ethoxy, propoxy or butoxy.

Acylamino as a phenyl substituent in $R_3$ and $R_4$ is, for example, acetylamino.

$A_3$—$R_3$ and $A_4$—$R_4$ as halogen are preferably fluorine and especially chlorine.

B as an aromatic bridge member is, for example, a radical of the formula

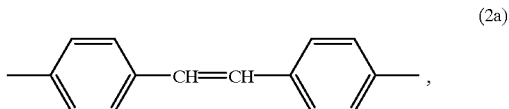

(2a)

(2b)

(2c)

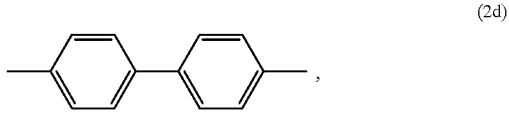

(2d)

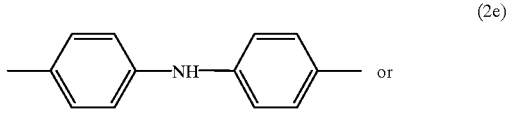

(2e)

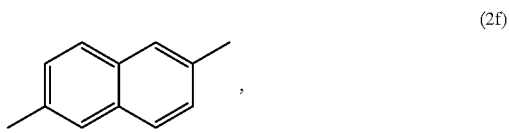

(2f)

in which formulae (2a) to (2f) the phenyl radicals may be mono- or poly-substituted by sulfo.

$R_1$ and $R_2$ as halogen are each independently of the other fluorine or chlorine.

$R_1$ is preferably halogen, especially chlorine.

$R_2$ is preferably halogen, especially chlorine.

$R_3$ is preferably a phenyl radical substituted by $C_1$-$C_4$alkyl, $C_1$-$C_4$alkoxy, acylamino, sulfo, —$SO_2$—$CH=CH_2$, —$SO_2$—$CH_2CH_2$—$OSO_3H$, —NH—CO—$CBr=CH_2$ or by —NH—CO—$CHBr$—$CH_2Br$, the phenyl radical being mono- or poly-substituted by the substituents mentioned.

There is preferred as $R_4$ a phenyl radical substituted by $C_1$-$C_4$alkyl, $C_1$-$C_4$alkoxy, acylamino, sulfo, —$SO_2$—$CH=CH_2$, —$SO_2$—$CH_2CH_2$—$OSO_3H$, —NH—CO—$CBr=CH_2$ or by —NH—CO—$CHBr$—$CH_2Br$, the phenyl radical being mono- or poly-substituted by the substituents mentioned.

$A_1$ is preferably —$NR_5$—.
$A_2$ is preferably —$NR_5$—.
$A_3$ is preferably —$NR_5$—.
$A_4$ is preferably —$NR_5$—.
$R_5$ is preferably hydrogen.

Compounds of formula (1) that are of importance for the process according to the invention are those wherein $A_1$, $A_2$, $A_3$ and $A_4$ are —NH—, B is a radical of the formula (3a) 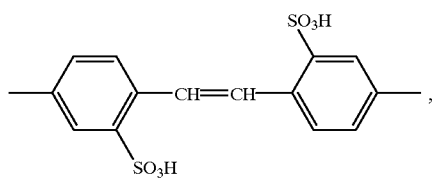
(3b) 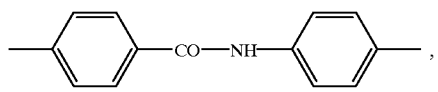
(3c) 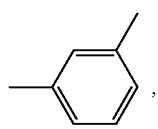
(3d) 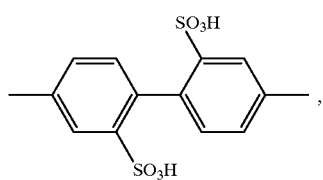
(3e) 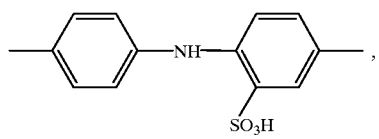
(3f) 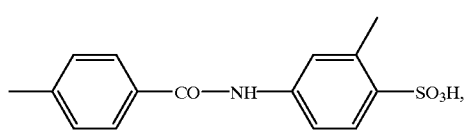
(3g) 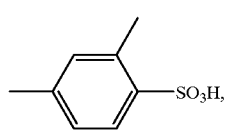
(3h) 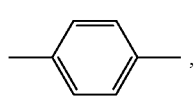
(3i) —CH$_2$—CH(CH$_3$)— or
(3j) 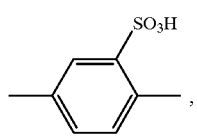
$R_1$ is chlorine, fluorine or
(3k) 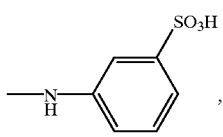
$R_2$ is chlorine or fluorine, $R_3$ is a radical of the formula
(4a) 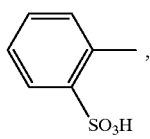
(4b) 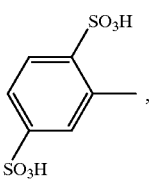
(4c) 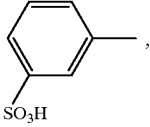
(4d) 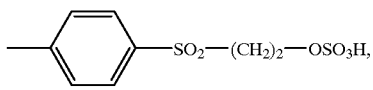
(4e) 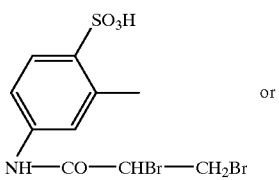 or
(4f) 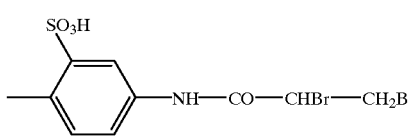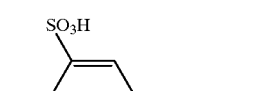
and $R_4$ is a radical of formula (4a), (4b), (4d), (4e), (4f),
(4g) 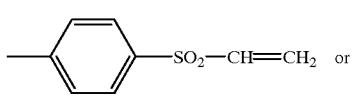 or -continued
(4h)
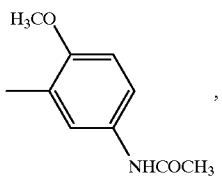
or A₃–R₃ and/or A₄–R₄ are/is chlorine.
Compounds that are of particular importance for the process according to the invention are the compounds of formulae
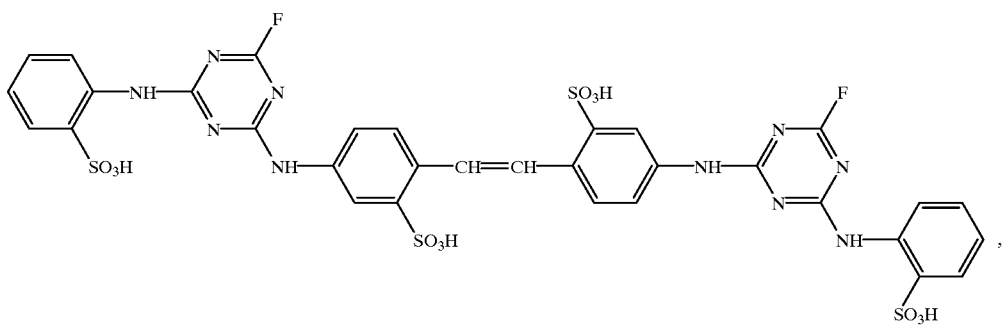
(100)
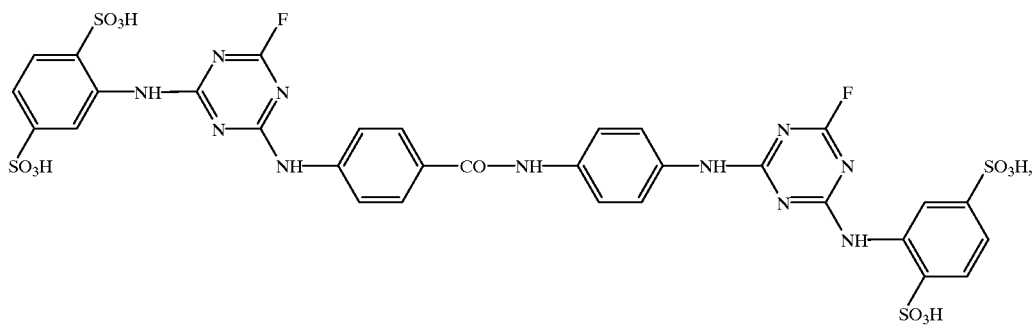
(101)
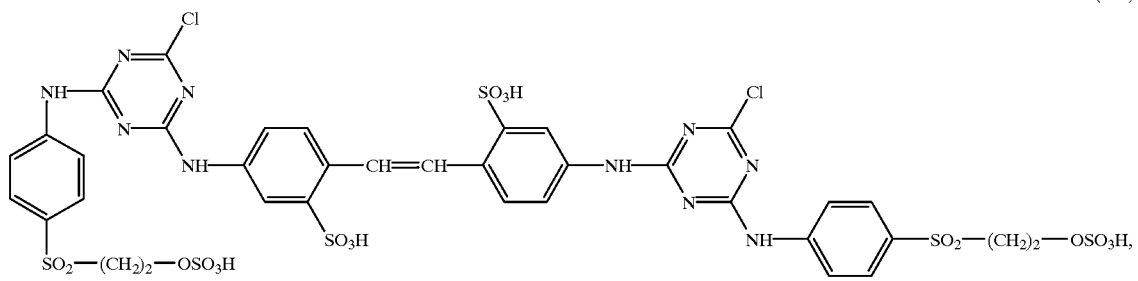
(102)

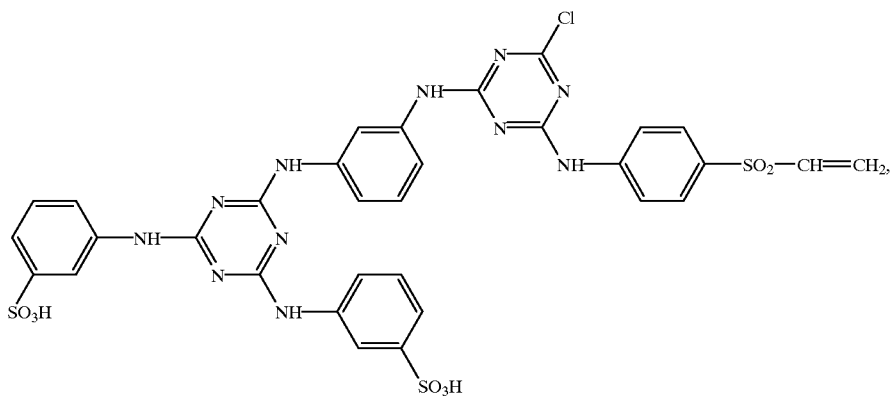
(103)
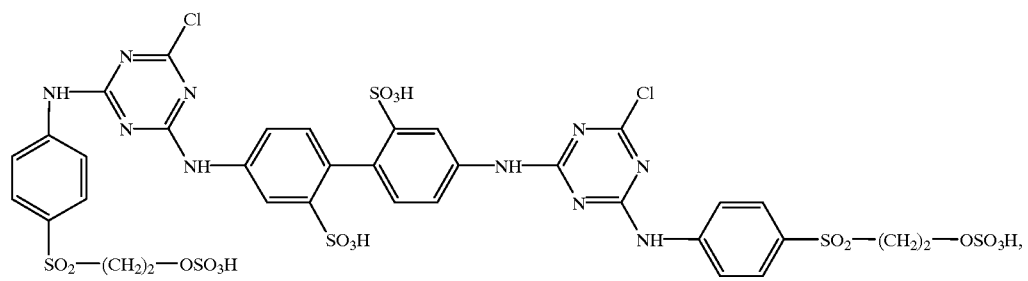
(104)
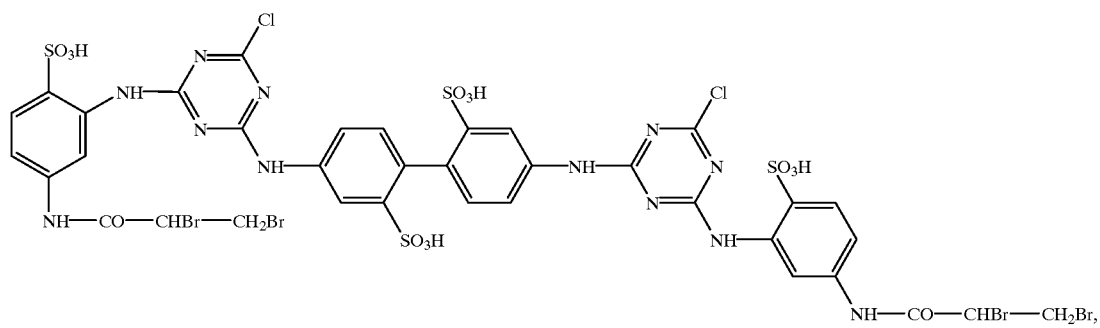
(105)
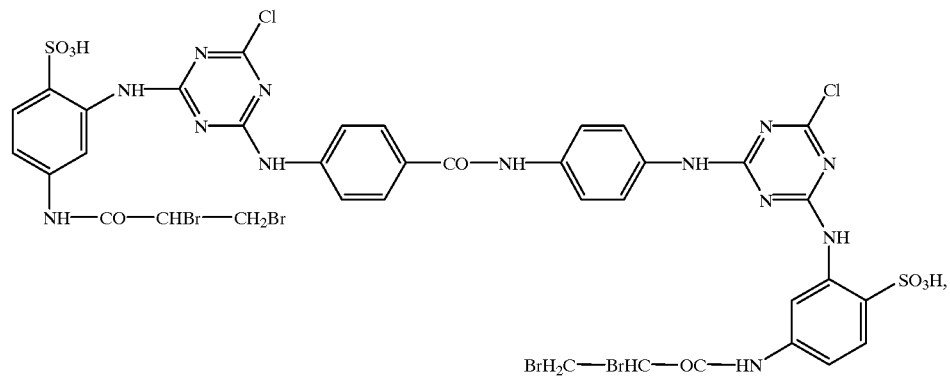
(106)

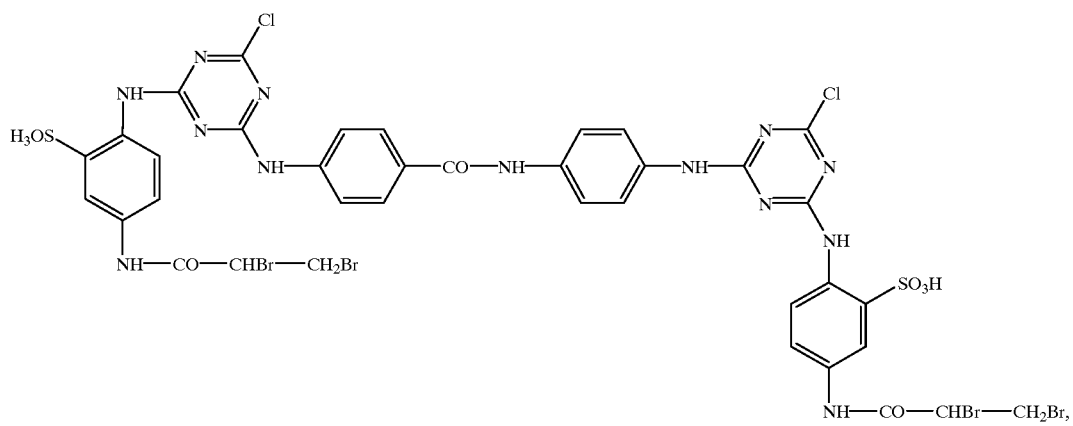
(107)
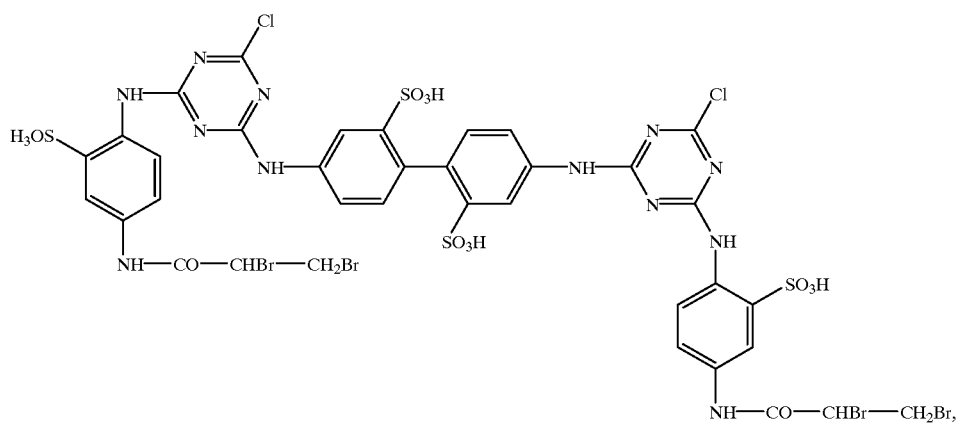
(108)
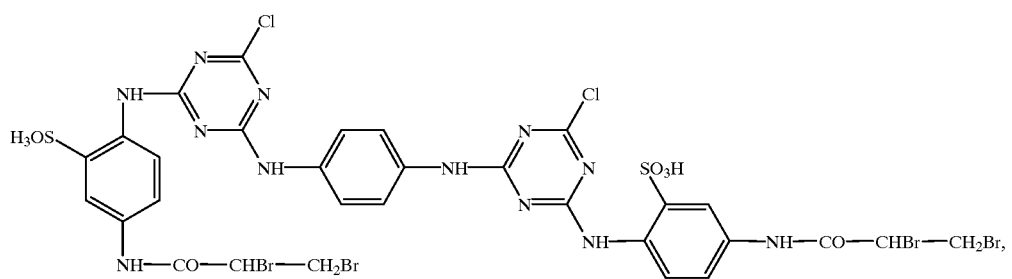
(109)
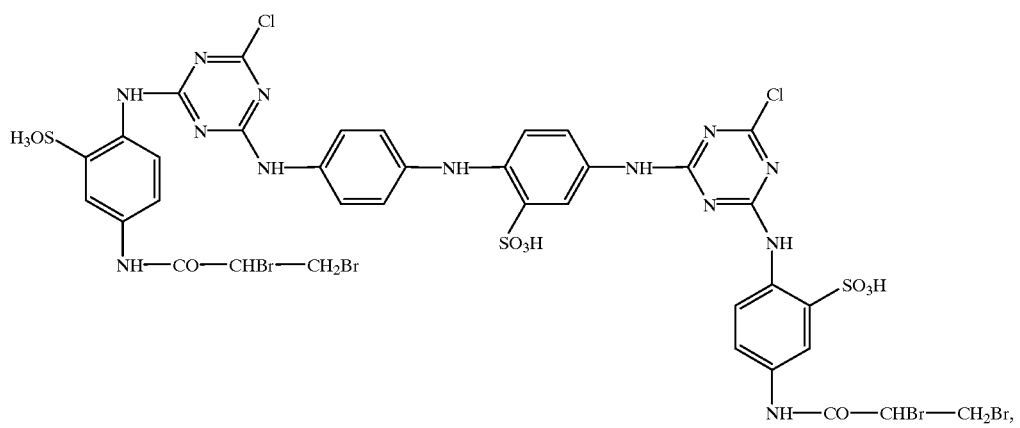
(110)

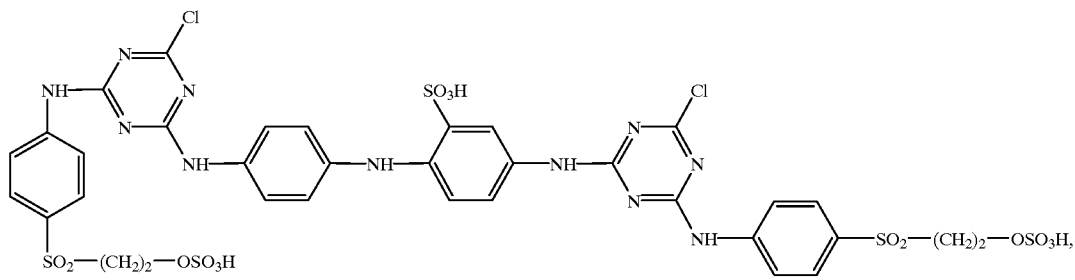
(111)
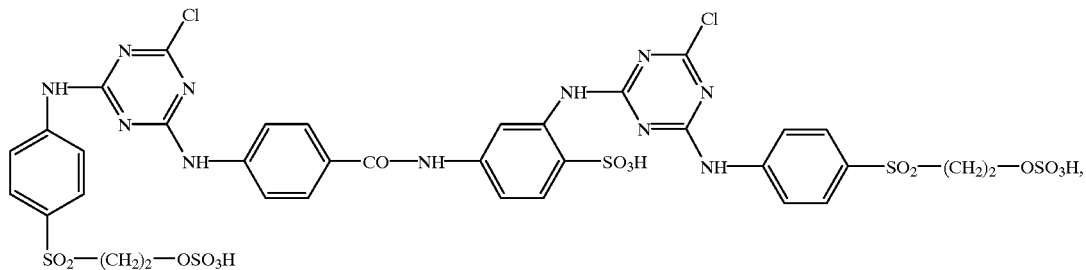
(112)
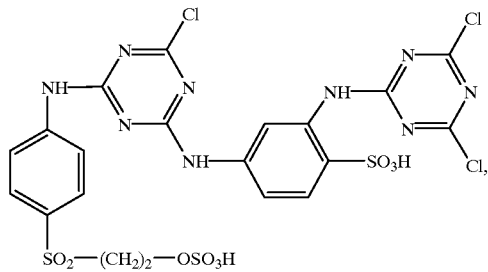
(113)
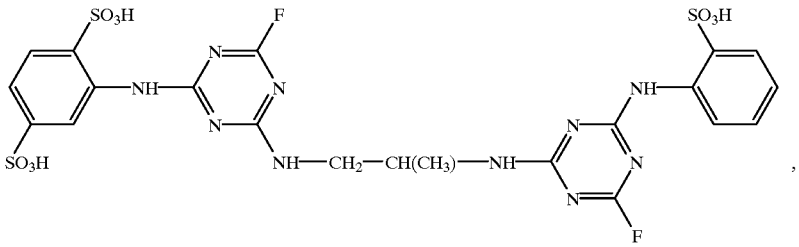
(114)
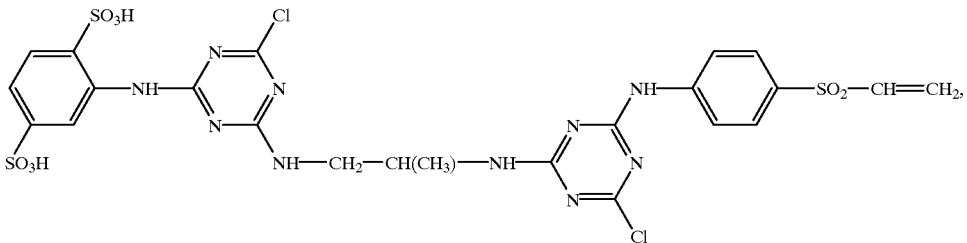
(115)

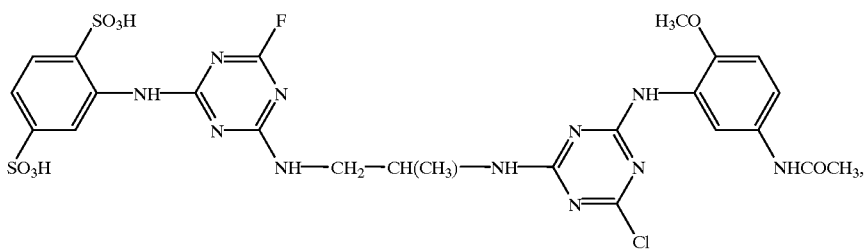
(116)

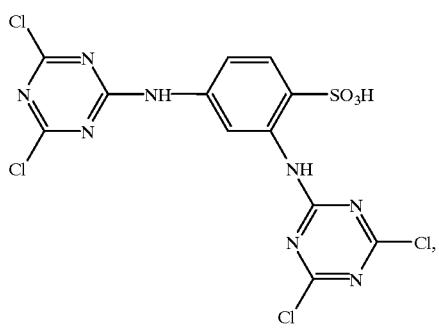
(117)

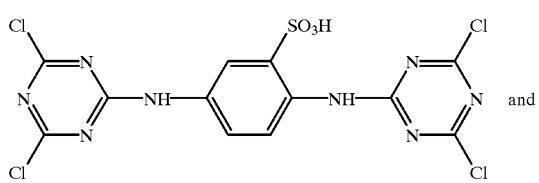
and
(118)

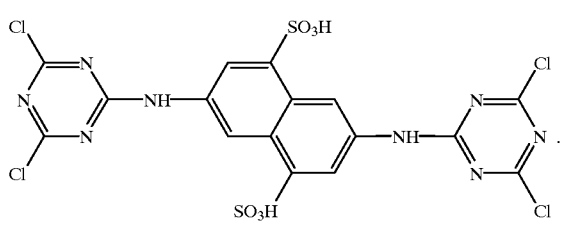
(119)

Compounds that are more especially important for the process according to the invention are the compounds of formulae (100), (101), (102), (103), (105), (108), (114), (117), (118) and (119).

The compounds of formulae (100), (101), (103), (105) to (116) and (119) are novel and the present invention relates also thereto.

The preparation of the compounds of formula (1) used in the process according to the invention is carried out according to methods known per se, for example by reacting a trichlorotriazine of the formula

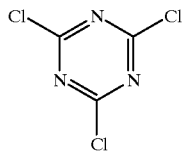
(5)

or a trifluorotriazine of the formula

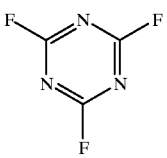
(5a)

with an equimolar amount of a compound of the formula $$R_3—A_3H \tag{6},$$

wherein $R_3$ and $A_3$ are as defined for formula (1), and then with a compound of the formula $$HA_1—B—A_2—H \tag{7},$$

wherein $A_1$, $A_2$ and B are as defined for formula (1), to form an intermediate of the formula

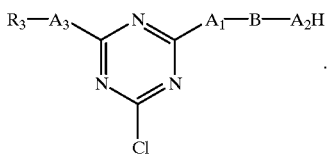 (8)

Subsequently, a second trichlorotriazine of formula (5) or a second trifluorotriazine of formula (5a) is, where appropriate, reacted with an equimolar amount of a compound of the formula $R_4—A_4H$ (9), wherein $A_4$ and $R_4$ are as defined for formula (1), and then with the intermediate of formula (8), and the resulting compound of the formula (10)

$$R_3—A_3\underset{\underset{Cl}{}}{\overset{}{\text{triazine}}}A_1—B—A_2\underset{\underset{Cl}{}}{\overset{}{\text{triazine}}}A_4—R_4$$

or of the formula (10a)

$$R_3—A_3\underset{\underset{F}{}}{\overset{}{\text{triazine}}}A_1—B—A_2\underset{\underset{F}{}}{\overset{}{\text{triazine}}}A_4—R_4$$

is isolated.

Alternatively, for example, a trichlorotriazine of formula (5) or a trifluorotriazine of formula (5a) is reacted with a compound of formula (7) in a molar ratio of 2:1.

The novel compounds of formulae (100), (101), (103), (105) to (116) and (119) are prepared in an analogous manner by reacting a trichlorotriazine of formula (5) with a compound of the formula (11)

[structure with SO₃H, NH₂, SO₃H on benzene ring]

(12)

[structure with NH₂ and SO₃H on benzene ring] or

-continued (13)

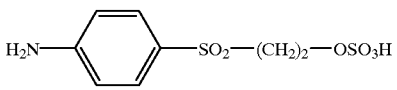

and then with a compound of the formula (14)

[structure: benzene with NH₂ and H₂N], (15)

[structure: benzene with NH₂, H₂N, SO₃H] or (16)

$H_2N—CH_2—CH(CH_3)—NH_2$, and condensing the resulting intermediate with a second trichlorotriazine of formula (5), which has, where appropriate, been reacted beforehand with a compound of the formula (17)

[structure: H₂N—C₆H₄—SO₂—CH=CH₂]

(18)

[structure with H₃CO, H₂N, NHCOCH₃], or, when $A_3—R_3=A_4—R_4$, reacting a trichlorotriazine of formula (5) with a compound of formula (13), (19)

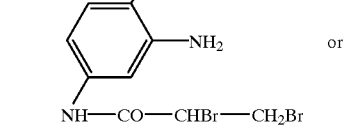 or (20)

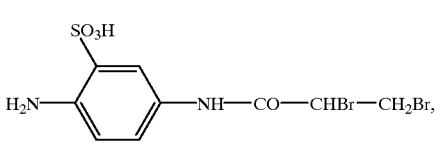

and condensing the resulting intermediate with a compound of the formula

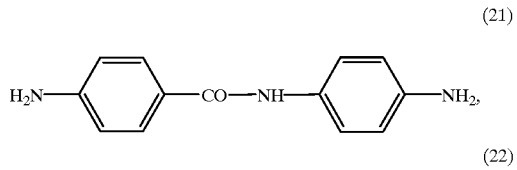

(21)

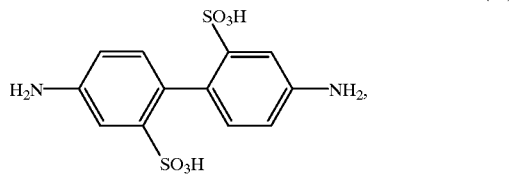

(22)

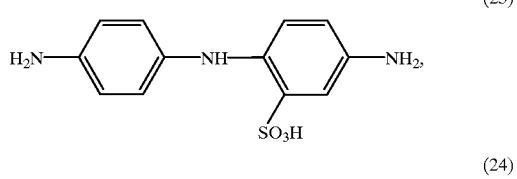

(23)

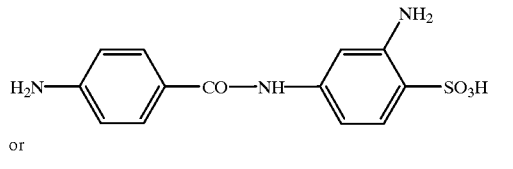

(24)

or

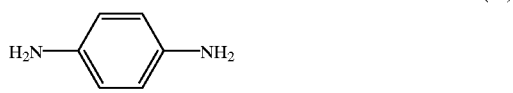

(25)

in a molar ratio of 2:1, or, when $A_3$—$R_3$=$A_4$—$R_4$=halogen, condensing a trichlorotriazine of formula (5) with a compound of formula (15) or

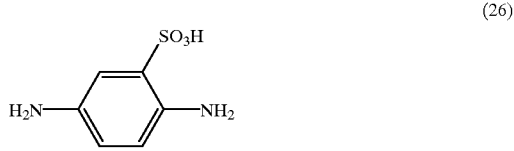

(26)

in a molar ratio of 2:1, or reacting a trifluorotriazine of formula (5a) with a compound of the formula

(11)

and then with a compound of formula (16), and condensing the resulting intermediate with a second trifluorotriazine of formula (5a), which has been reacted beforehand with a compound of the formula

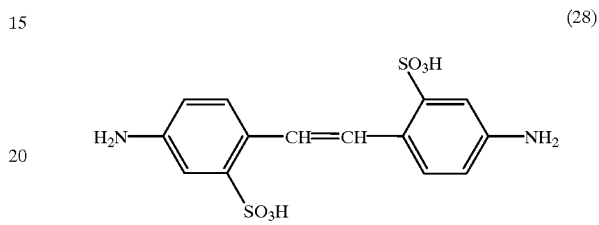

(27)

or, when $A_3$—$R_3$=$A_4$—$R_4$, reacting a trifluorotriazine of formula (5a) with a compound of formula (27) or (11), and condensing the resulting intermediate with a compound of the formula (28)

or (21) in a molar ratio of 2:1.

Compounds of formulae (11) to (28) are known and can be prepared according to methods known per se.

An advantageous embodiment of the process according to the invention comprises treating the lyocell cellulose fibres with the compounds used in accordance with the invention in an alkaline medium.

The alkaline medium is preferably formed by an alkali metal carbonate and/or an alkali metal hydroxide, such as, for example, sodium carbonate, sodium hydroxide or potassium hydroxide.

The treatment can be performed either on undyed fibres, or on fibres that are to be dyed, before, during or immediately after a dyeing process. Where the compounds used in accordance with the invention are applied to undyed fibres, they may be applied either by means of a treatment bath or immediately after the spinning operation to the freshly spun fibres that have not yet been dried (so-called "never-dried" fibres, as described, for example, in EP-A-0 538 977, page 4, or in U.S. Pat. No. 5,580,354, column 4).

Where the compounds used in accordance with the invention are applied in the course of a dyeing process, their application advantageously takes place before or during the actual dyeing operation.

In that case, the compounds used in accordance with the invention may be applied to the fibres in a separate treatment bath or, preferably, together with the dyes being used, in a dyeing bath under the relevant dyeing conditions.

Where the compounds used in accordance with the invention are applied to the fibres from a separate treatment bath, this may be carried out at a temperature of from 15 to 140° C., preferably from 40 to 100° C., for a period of from 10 to 120 minutes, preferably from 30 to 90 minutes. A further advantageous embodiment of the process according to the invention comprises wetting the fibres with an aqueous solution of the compounds used in accordance with the invention and then subjecting them to steam treatment at from 90 to 130° C. for a period of from 5 to 60, preferably from 10 to 30, seconds.

The fibres can be wetted either by immersion in a bath or by spraying.

The lyocell cellulose fibres may be in the form of fibres, in the form of yarn, or in the form of flat goods, such as, for example, woven fabrics, knitted fabrics or webs, and may be treated in any of those forms.

The compounds used in accordance with the invention are normally employed in the treatment bath or dye bath in amounts of from 0.1 to 15% by weight, especially from 1 to 10% by weight, more especially from 2 to 6% by weight, based on the weight of the fibres.

The present invention relates also to the use of the compounds of formula (1) for reducing fibrillation in lyocell cellulose. The fibrillation tendency of the untreated and treated fibres is assessed according to a modified Martindale abrasion test, in which a wetted specimen of fabric is abraded under a defined load until a hole forms. The number of abrasion cycles taken for a hole to be formed gives the resistance to wet abrasion, which serves as a measure of the fibrillation.

The following Examples serve to illustrate the invention. The temperatures are given in degrees Celsius, parts are parts by weight, and percentages relate to percent by weight, unless otherwise indicated. Parts by weight relate to parts by volume in a ratio of kilograms to liters.

EXAMPLE 1

In a laboratory reaction vessel, 14.35 g of aniline-2,5-disulfonic acid are dissolved and neutralised in 100 parts of water, 1 g of sodium dihydrogen phosphate is added and the mixture is cooled to 0° C. With intensive stirring, 4.5 ml of cyanuric fluoride are added dropwise thereto over a period of 10 minutes, and the temperature is maintained at 0° C. by cooling. The pH is maintained at 6.0 by metering in 5N aqueous sodium hydroxide solution. When the condensation is complete, a solution of 3.7 g of 1,2-diaminopropane in 25 ml of water and 5 ml of 10N hydrochloric acid are added, and the mixture is left to condense at from 2 to 5° C. and pH 6.0 for 5 hours, the pH being maintained at 6.0 by means of a 5N aqueous sodium hydroxide solution. This results in a compound of the formula

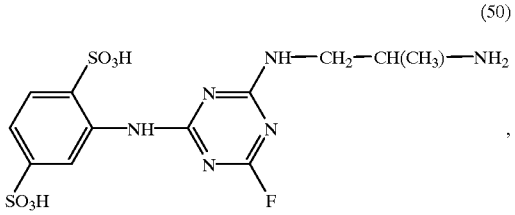

(50)

which is obtained as an intermediate in good yield and with a high degree of purity in the form of a solution. In a separate glass beaker, 8.6 g of aniline-2-sulfonic acid are stirred in 100 parts of water and dissolved and neutralised with 10 ml of a 5N aqueous sodium hydroxide solution.

With very intensive stirring, 4.5 ml of cyanuric fluoride are then added dropwise at 0° C., within a period of 10 minutes, while a pH of 6 is maintained. The condensation is complete after 10 minutes stirring.

The resulting solution is added to the above-described solution of the compound of formula (50), and the pH is adjusted to and maintained at 9.0. The temperature is increased to 15° C. within a period of 30 minutes. A solution of the compound of the formula

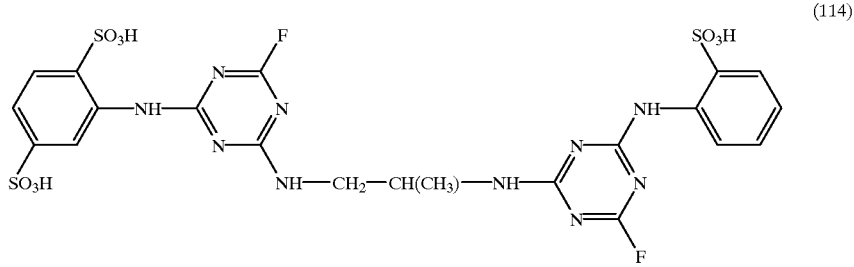

(114)

is obtained. 1.8 g of sodium tripolyphosphate buffer are added to that solution, and the resulting solution is freeze-dried at pH 7.5.

42 g of a white, readily water-soluble powder of the compound of formula (114) are obtained.

EXAMPLES 2 TO 5

By proceeding as indicated in Example 1, but using instead of cyanuric fluoride an equimolar amount of cyanuric chloride, instead of aniline-2,5-disulfonic acid an equimolar amount of a compound of formula )11) to (13), instead of 1,2-diaminopropane where appropriate an equimolar amount of a compound of formula (15) or (25), and instead of aniline-2-sulfonic acid an equimolar amount of a compound of formula (17) or (18), the compounds of formulae (103), (113), (115) and (116) listed in Table 1 are obtained.

TABLE 1

| Compound of formula | No. | Compound of formula | No. | Compound of formula | No. | Compound of formula |
|---|---|---|---|---|---|---|
| 2-aminobenzenesulfonic acid (3-amino, SO₃H) | (12) | H₂N—C₆H₄—NH₂ (para) | (25) | H₂N—C₆H₄—SO₂CH=CH₂ | (17) | (103) |
| H₂N—C₆H₄—SO₂(CH₂)₂OSO₃H | (13) | 2,4-diaminobenzenesulfonic acid | (15) | — | — | (113) |
| 2-amino-1,4-benzenedisulfonic acid | (11) | 1,2-diaminopropane | — | H₂N—C₆H₄—SO₂CH=CH₂ | (17) | (115) |
| 2-amino-1,4-benzenedisulfonic acid | (11) | 1,2-diaminopropane | — | 2-methoxy-5-acetamidoaniline (H₃CO, NH₂, NHCOCH₃) | (18) | (116) |

EXAMPLE 6

In a laboratory reaction vessel, 9.4 g of cyanuric chloride are stirred intensively at 0° C., for one hour, together with 100 g of ice-water, 0.1 g of a commercially available surface-active auxiliary and 1.1 g of sodium dihydrogen phosphate as buffer.

In a second laboratory reaction vessel, 14 g of a compound of the formula

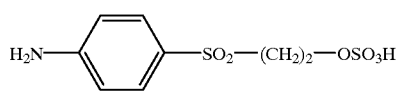

(13)

in 150 ml of water containing 5.3 g of sodium carbonate are dissolved at a pH of 6.0 and a temperature of 30° C. to form a clear solution. The solution is cooled to approximately 0° C. and then added to the cyanuric chloride suspension. The mixture is subsequently stirred at pH 6.0 at a temperature of from 0 to 2° C. until the compound of formula (13) can no longer be detected by a HPLC assay.

9.2 g of a compound of the formula

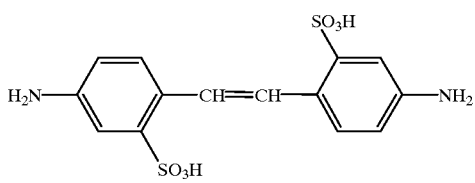

(28)

are then added to the above mixture, and the temperature is slowly increased to approximately from 30 to 35° C., the pH value again being maintained at 6.0.

To complete the condensation, stirring is continued for about 30 minutes more at from 30 to 35° C.

The reaction solution is then desalted by dialysis and subsequently freeze-dried.

37 g of a light-coloured powder of the compound of the formula (102)

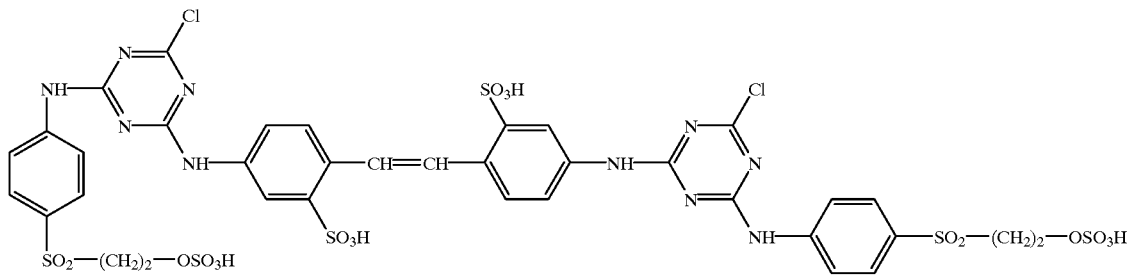

are obtained.

EXAMPLE 7

By proceeding as indicated in Example 6, but using instead of cyanuric chloride an equimolar amount of cyanuric fluoride, and instead of the compound of the formula (13) an equimolar amount of the compound of formula (27), the compound of formula (100) is obtained.

EXAMPLE 8

By proceeding as indicated in Example 6, but using instead of cyanuric chloride an equimolar amount of cyanuric fluoride, instead of the compound of formula (13) an equimolar amount of the compound of formula (11) and instead of the compound of formula (28) an equimolar amount of the compound of formula (21), the compound of formula (101) is obtained.

EXAMPLES 9 TO 11

By proceeding as indicated in Example 6, but using instead of the compound of formula (28) an equimolar amount of a compound of formula (22), (23) or (24), the compounds of formulae (104), (111) and (112) are obtained.

EXAMPLES 12 TO 17

By proceeding as indicated in Example 6, but using instead of the compound of formula (28) an equimolar amount of a compound of formula (21), (22), (23) or (25), and instead of the compound of formula (13) an equimolar amount of a compound of formula (19) or (20), the compounds of formulae (105) to (110) listed in Table 2 are obtained.

TABLE 2

| Compound of formula | No. | Compound of formula | No. | Compound of formula No. |
|---|---|---|---|---|
| ![structure with SO3H, NH2, NH-CO-CHBr-CH2Br] | (19) | $H_2N$-⌬-CONH-⌬-$NH_2$ | (21) | (106) |
| ![structure with SO3H, H2N, NHCOCHBr-CH2Br] | (20) | $H_2N$-⌬-CONH-⌬-$NH_2$ | (21) | (107) |
| ![structure with SO3H, NH2, NH-CO-CHBr-CH2Br] | (19) | ![biphenyl with SO3H groups and NH2 groups] | (22) | (105) |

TABLE 2-continued

| Compound of formula | No. | Compound of formula | No. | Compound of formula No. |
|---|---|---|---|---|
| 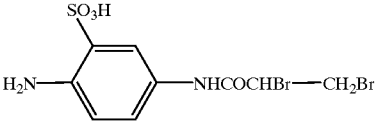 | (20) | 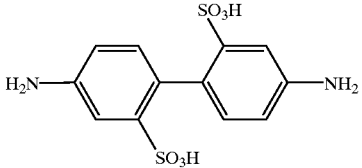 | (22) | (108) |
| 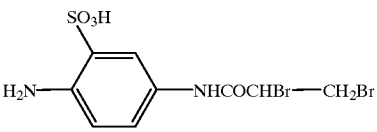 | (20) |  | (25) | (109) |
| 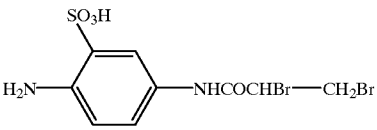 | (20) | 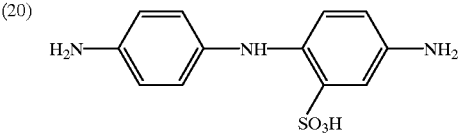 | (23) | (110) |

EXAMPLE 18

A liquor consisting of 50 ml of water and 15 ml of an aqueous 20% sodium sulfate solution is introduced into a laboratory dyeing apparatus and heated to 50° C. A piece of 10 g lyocell fabric is then immersed in the liquor and the temperature is increased to 90° C. at a rate of 2° C./min. During the heating phase, 0.6 g of the compound of formula (114), dissolved in 27.5 ml of water, is added at 70° C. The lyocell fabric is treated at 90° C. for 60 minutes. The treatment liquor is then cooled to 70° C., 7.5 ml of an aqueous 20% sodium carbonate solution are added, and the mixture is maintained at 70° C. for a further 45 minutes.

The bath is then drawn off and the treated lyocell fabric is rinsed with water, boiled for 5 minutes in fresh bath consisting of water only, cold-rinsed again and dried.

In a Martindale abrasion test, the dried lyocell fabric withstands approximately 1.5 times the number of abrasion cycles compared with untreated lyocell fabric.

With this manner of application, the lyocell fabric can simultaneously also be dyed by adding one or more reactive dyes immediately after the addition of the compound of formula (114).

By proceeding as described in Example 18, but using instead of 0.6 g of the compound of formula (114) the same amount of a compound of formula (100) to (113) or (115) to (118), a lyocell fabric having high Martindale abrasion test values is likewise obtained.

EXAMPLE 19

A liquor consisting of 50 ml of water and 15 ml of an aqueous 20% sodium sulfate solution is introduced into a laboratory dyeing apparatus and heated to 60° C. A piece of 10 g lyocell fabric is then immersed in the liquor and 3 minutes later 0.6 g of the compound of formula (113), dissolved in 25.5 ml of water, is added. After a further 15 minutes, 7.5 ml of an aqueous 20% sodium carbonate solution are added to the liquor. The liquor is then maintained at 60° C. for 30 minutes.

2 ml of an aqueous 3% sodium hydroxide solution are then added to the liquor, which is maintained at 60° C. for a further 10 minutes, and the lyocell fabric is then finished as described in Example 18.

The finished lyocell fabric can then be dyed according to conventional methods using, for example, reactive dyes.

In a Martindale abrasion test, the dried lyocell fabric withstands approximately 1.5 times the number of abrasion cycles compared with untreated lyocell fabric.

By proceeding as described in Example 19, but using instead of 0.6 g of the compound of formula (113) the same amount of a compound of formula (100) to (112) or (114) to (118), a lyocell fabric having high Martindale abrasion test values is likewise obtained.

EXAMPLE 20

A lyocell fabric is pad-dyed with an aqueous liquor containing 42 g/l of a compound of the formula (100)

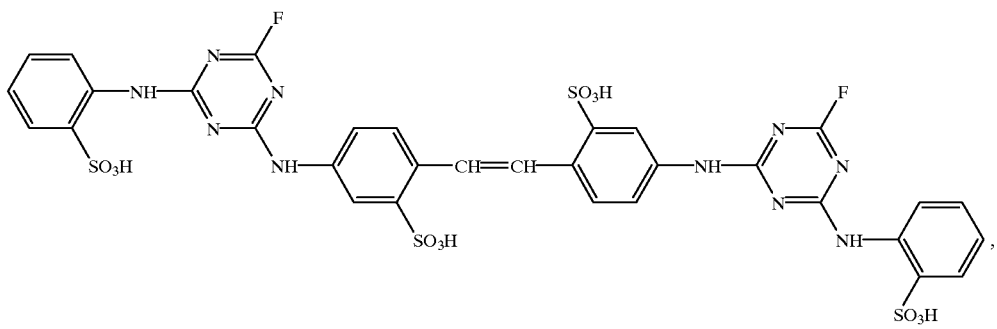

30 g/l of calcined sodium carbonate and 1 g/l of a commercially available wetting agent, (liquor pick-up 70%). The lyocell fabric so treated is further treated directly, without being dried, in saturated steam of a temperature of 102° C. for 8 minutes. The lyocell fabric is then rinsed with water, boiled for 5 minutes in fresh bath consisting of water only, cold-rinsed and dried.

In a Martindale abrasion test, the treated lyocell fabric withstands approximately twice the number of abrasion cycles compared with untreated lyocell fabric.

By proceeding as described in Example 19, but using instead of 42 g of the compound of formula (100) the same amount of a compound of formula (101) to (119), a lyocell fabric having high Martindale abrasion test values is likewise obtained.

What is claimed is:

1. A process for the treatment of lyocell cellulose fibres which comprises treating the lyocell cellulose fibres with at least one compound of the formula

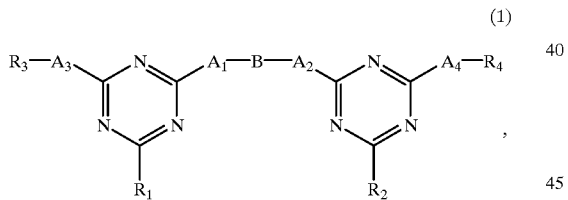

(1)

wherein $R_1$ and $R_2$ are each independently of the other halogen or a sulfo-substituted phenylamino radical, at least one of the two substituents $R_1$ and $R_2$ being halogen, $R_3$ and $R_4$ are each independently of the other unsubstituted phenyl or phenyl substituted by $C_1$–$C_4$alkyl, $C_1$–$C_4$alkoxy, acylamino, sulfo, —$SO_2$—CH=$CH_2$, —$SO_2$—$CH_2CH_2$—$OSO_3H$, —NH—CO—CBr=$CH_2$ or by —NH—CO—CHBr—$CH_2$Br, $A_1$ and $A_2$ are each independently of the other —O—, —S— or —$NR_5$—, wherein $R_5$ is hydrogen or $C_1$–$C_4$alkyl, $A_3$ and $A_4$ are each independently of the other —O—, —S— or —$NR_5$—, or —$A_3$—$R_3$ is halogen and/or —$A_4$—$R_4$ is halogen, wherein $R_5$ is hydrogen or $C_1$–$C_4$alkyl and B is an aromatic bridge member, or —$A_1$—B—$A_2$— is a bridge member of the formula —NH—$CH_2$—CH($CH_3$)—NH—, with the proviso that the compound of formula (1) must contain at least one dihalotriazine radical, at least two monohalotriazine radicals or at least one substituent selected from the group consisting of —$SO_2$—CH=$CH_2$, —$SO_2$—$CH_2CH_2$—$OSO_3H$, —NH—CO—CBr=$CH_2$ and —NH—CO—CHBr—$CH_2$Br.

2. A process according to claim 1, wherein the compound of formula (1) contains at least two identical or different substituents selected from the group consisting of —$SO_2$—CH=$CH_2$, —$SO_2$—$CH_2CH_2$—$OSO_3H$, —NH—CO—CBr=$CH_2$ and —NH—CO—CHBr—$CH_2$Br.

3. A process according to claim 1, which comprises treating the lyocell cellulose fibres with at least one compound of formula (1) wherein B is a radical of the formula

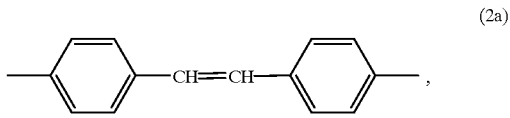

(2a)

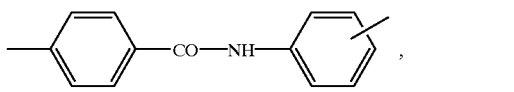

(2b)

(2c)

(2d)

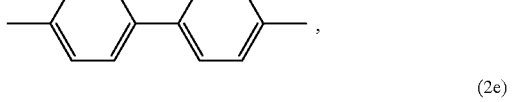

(2e)

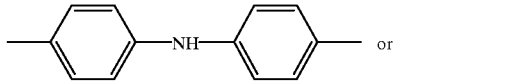

(2f)

in which formulae (2a) to (2f) the phenyl radicals are optionally mono- or poly-substituted by sulfo.

4. A process according to claim 1, which comprises treating the lyocell cellulose fibres with at least one compound of formula (1) wherein $A_1$, $A_2$, $A_3$ and $A_4$ are —NH—, B is a radical of the formula (3a) 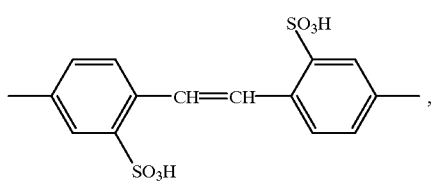
(3b) 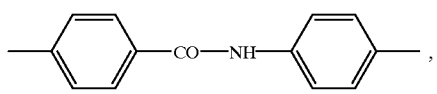
(3c) 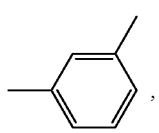
(3d) 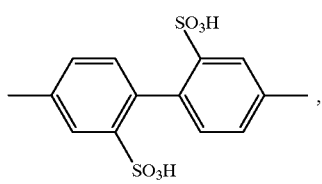
(3e) 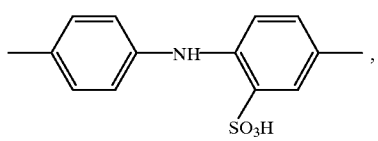
(3f) 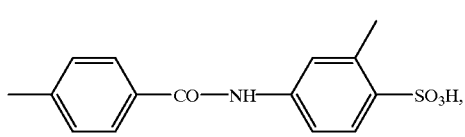
(3g) 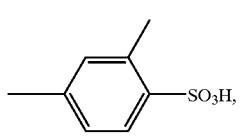
(3h) 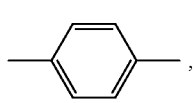
(3i) —CH$_2$—CH(CH$_3$)— or
(3j) 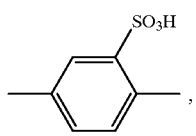
$R_1$ is chlorine, fluorine or
(3k) 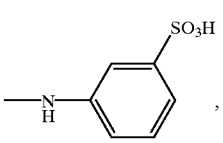
$R_2$ is chlorine or fluorine, $R_3$ is a radical of the formula
(4a) 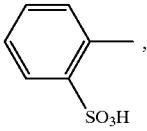
(4b) 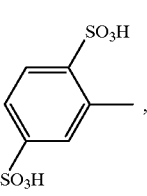
(4c) 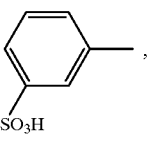
(4d) 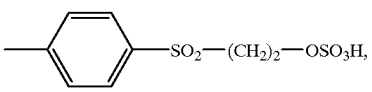
(4e) 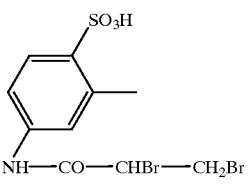
(4f) 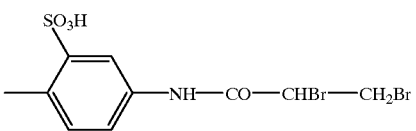
and $R_4$ is a radical of formula (4a), (4b), (4d), (4e), (4f),
(4g) 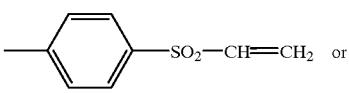

-continued

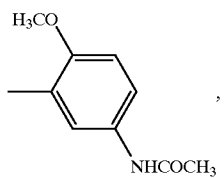
(4h)

or A$_3$—R$_3$ and/or A$_4$—R$_4$ are/is chlorine.

5. A process according to claim 1, which comprises using from 0.1 to 15% by weight of a compound of formula (1) based on the weight of the fibres.

6. A process according to claim 1, which comprises applying a compound of formula (1) to freshly spun fibres that have not yet been dried.

7. A process according to claim 1, which comprises applying a compound of formula (1) to the fibres before or during a dyeing process.

* * * * *